(12) United States Patent
Skalinski et al.

(10) Patent No.: US 9,097,821 B2
(45) Date of Patent: Aug. 4, 2015

(54) INTEGRATED WORKFLOW OR METHOD FOR PETROPHYSICAL ROCK TYPING IN CARBONATES

(75) Inventors: Mark Skalinski, San Ramon, CA (US); Jeroen Kenter, Oakland, CA (US)

(73) Assignee: CHEVRON U.S.A. INC., San Ramon, CA (US)

( * ) Notice: Subject to any disclaimer, the term of this patent is extended or adjusted under 35 U.S.C. 154(b) by 625 days.

(21) Appl. No.: 13/347,512

(22) Filed: Jan. 10, 2012

(65) Prior Publication Data

US 2013/0179080 A1    Jul. 11, 2013

(51) Int. Cl.
  *G01V 1/30* (2006.01)
  *E21B 49/00* (2006.01)
  *G01V 99/00* (2009.01)
  *G01N 15/08* (2006.01)

(52) U.S. Cl.
  CPC ............ *G01V 99/00* (2013.01); *G01N 15/0886* (2013.01)

(58) Field of Classification Search
  CPC ..... E21B 49/00; E21B 47/00; G06F 17/5009; G06F 2217/10; G06F 2217/16; G01V 1/44; G01V 99/00; G01N 15/0886
  USPC .......................... 702/7, 11, 189; 706/8, 21, 46
  See application file for complete search history.

(56) References Cited

U.S. PATENT DOCUMENTS

| | | | | |
|---|---|---|---|---|
| 4,821,164 A | * | 4/1989 | Swanson | 702/5 |
| 4,991,095 A | * | 2/1991 | Swanson | 702/16 |
| 5,012,674 A | * | 5/1991 | Millheim et al. | 73/152.03 |
| 5,109,697 A | * | 5/1992 | Millheim et al. | 73/152.11 |
| 5,395,768 A | * | 3/1995 | Nery | 436/25 |
| 6,115,671 A | * | 9/2000 | Fordham et al. | 702/8 |
| 6,721,661 B2 | * | 4/2004 | Anstey et al. | 702/8 |
| 6,977,499 B2 | * | 12/2005 | Kiesl et al. | 324/303 |
| 7,472,588 B2 | * | 1/2009 | Slavin et al. | 73/152.11 |
| 8,282,484 B2 | * | 10/2012 | Toriyama | 463/37 |
| 8,311,788 B2 | * | 11/2012 | Hurley et al. | 703/9 |
| 8,339,648 B2 | * | 12/2012 | Torii et al. | 358/1.15 |
| 8,352,228 B2 | * | 1/2013 | Walters et al. | 703/10 |
| 8,725,477 B2 | * | 5/2014 | Zhang et al. | 703/10 |
| 2003/0231017 A1 | * | 12/2003 | Kiesl et al. | 324/303 |
| 2007/0246649 A1 | * | 10/2007 | Jacobi et al. | 250/269.6 |
| 2008/0257530 A1 | * | 10/2008 | Burk et al. | 165/104.19 |
| 2009/0259446 A1 | * | 10/2009 | Zhang et al. | 703/2 |

(Continued)

OTHER PUBLICATIONS

G. E. Archie, "Classification of Carbonate Reservoir Rocks and Petrophysical Considerations," Bulletin of the American Association of Petroleum Geologists, vol. 36, No. 2 (Feb. 1952), pp. 278-298.

(Continued)

*Primary Examiner* — Carol S Tsai
(74) *Attorney, Agent, or Firm* — Albert K. Shung

(57) ABSTRACT

Disclosed are various embodiments of a workflow or method for petrophysical rock typing of carbonates in an oil or gas reservoir or field comprising determining a Data Scenario (DS) for the reservoir or field, determining a plurality of Depositional Rock Types (DRTs) for the reservoir or field, determining a Digenetic Modification (DM) from a plurality of diagenetic modifiers or primary textures associated with the plurality of DRTs, selecting a Reservoir Type (RT) corresponding to the plurality of DRTs, determining at least one pore type, and determining, on the basis of the plurality of DRTs, the Diagenetic Modification (DM), and the at least one pore type, a plurality of Petrophysical Rock Types (PRTs) associated with the RT.

41 Claims, 13 Drawing Sheets

(56) References Cited

U.S. PATENT DOCUMENTS

| | | | |
|---|---|---|---|
| 2009/0271116 A1* | 10/2009 | Norris et al. | 702/11 |
| 2010/0009839 A1* | 1/2010 | Can et al. | 501/87 |
| 2010/0161302 A1* | 6/2010 | Walters et al. | 703/12 |
| 2011/0066404 A1* | 3/2011 | Salazar-Tio et al. | 703/1 |
| 2011/0102833 A1* | 5/2011 | Torii et al. | 358/1.15 |
| 2011/0295508 A1* | 12/2011 | Lee et al. | 702/11 |
| 2012/0197526 A1* | 8/2012 | Guerrero et al. | 702/2 |
| 2013/0006591 A1* | 1/2013 | Pyrcz et al. | 703/2 |
| 2013/0030777 A1* | 1/2013 | Sung et al. | 703/6 |
| 2013/0046524 A1* | 2/2013 | Gathogo et al. | 703/6 |

OTHER PUBLICATIONS

Choquette et al., "Geologic Nomenclature and Classification of Porosity in Sedimentary Carbonates," Bulletin of the American Association of Petroleum Geologists, vol. 54, No. 2 (Feb. 1970), pp. 207-250.

Robert J, Dunham, "Classification of Carbonate Rocks According to Depositional Texture," 1962.

Embry et al., "A Late Devonian Reef Tract on Northeastern Banks Island, N.W.T.," Bulletin of Canadian Petroleum Geology, vol. 19, No. 4 (Dec. 1971) pp. 730-761.

F. J. Lucia, "Petrophysical Parameters Estimated from Visual Descriptions of Carbonate Rocks: A Field Classification of Carbonate Pore Space," Society of Petroleum Engineers Annual Conference, Oct. 1981, pp. 629-637.

Lucia et al., "Predicting Permeability From Well Logs in Carbonates with a Link to Geology for Interwell Permeability Mapping," Society of Petroleum Engineers, Reservoir Evaluation and Engineering, Aug. 2003, pp. 215-225.

Marzouk et al. In "New Classification of Carbonate Rocks for Reservoir Characterization," of Petroleum Engineers SPE # 49475, 8th Abu Dhabi International Petroleum Conference, Oct. 1998.

Nelson, R.A. "Geologic Analysis of Naturally Fractured Reservoirs," 2nd ed. (2001), Gulf Publishing, Houston pp. 101-103.

Amaefule et al, "Enhanced Reservoir Description: Using Core and Log Data to Identify Hydraulic (Flow) Units and Predict Permeability in Uncored Intervals/Wells," Society of Petroleum Engineers, SPE 26436, 68th Annual Technical Conference, Houston, TX, Oct. 1993.

Arve Lønøy, "Making sense of carbonate pore systems," AAPG Bulletin, v. 90, No. 9 (Sep. 2006), pp. 1381-1405.

Clerke et al., "Multiple Discrete Pore Systems in Arab D Limestone," from oral presentation at AAPG Annual Convention, San Antonio, Texas, Apr. 20-23, 2008.

Ramakrishnan et al., "A Model-Based Interpretation Methodology for Evaluating Carbonate Reservoirs," Society of Petroleum Engineers, SPE # 71704, SPE Annual Technical Conference and Exhibition, New Orleans Sep. 2001.

Skalinski et al., "Rock Type Defmition and Pore Type Classification of a Carbonate Platform, Tengiz Field, Republic of Kazakhstan," SPWLA 50th Annual Logging Symposium, Jun. 2009.

Gunter et al., "Early Determination of Reservoir Flow Unites Using an Integrated Petrophysical Method," SPE # 38679, Society of Petroleum Engineers Annual Conference, Oct. 1997.

Cheng, Francisco et. al.; "Comparison of Petrophysical Rock Types from Core and Well-logs Using Post-stack 3D Seismic Data: Field Example from Maracaibo-Venezuela"; SEG Las Vegas 2008 Annual Meeting; pp. 1595-1599.

Hollis, Cathy et. al.; "Pore System Characterisation in Heterogeneous Carbonates: An Alternative Approach to Widely-used Rock-typing Methodologies"; Marine and Petroleum Geology, 2010, vol. 27, pp. 772-793.

Skalinski, Mark et. al.; "Carbonate Petrophysical Rock Typing: Integrating Geological Attributes and Petrophysical Properties While Linking with Dynamic Behavior"; Search and Discovery Article #120089; Jan. 22, 2013.

Sneider, R.M. et. al.; "Rock Types, Depositional History, and Diagenetic Effects, Ivishak Reservoir, Prudhoe Bay Field"; SPE Reservoir Engineering, Feb. 1997, pp. 23-30.

International Search Report, issued on Apr. 18, 2013 during the prosecution of International Application No. PCT/2013/020648.

\* cited by examiner

DATA SCENARIOS: DEFINITION AND TYPES

400

| DATA SCENARIO DEFINITION | | LOGGING SURVEYS | | | | |
|---|---|---|---|---|---|---|
| | | WELL DENSITY | LOG DATA QUALITY | COMPLETENESS | CORE DATA PRT REPRESENTATIVITY | DYNAMIC DATA COVERAGE |
| DATA SCENARIO | 3 | H | H | MODERN | ALL | H |
| | 2 | M | M | MIXED | PARTIAL | M |
| | 1 | L | L | VINTAGE | NONE | L |

DS 3

| | | LOGGING SURVEYS | | | | |
|---|---|---|---|---|---|---|
| | | WELL DENSITY | LOG DATA QUALITY | COMPLETENESS | CORE DATA PRT REPRESENTATIVITY | DYNAMIC DATA COVERAGE |
| DATA SCENARIO | 3 | H | H | MODERN | ALL | H |
| | 2 | M | M | MIXED | PARTIAL | M |
| | 1 | L | L | VINTAGE | NONE | L |

DS 2

| | | LOGGING SURVEYS | | | | |
|---|---|---|---|---|---|---|
| | | WELL DENSITY | LOG DATA QUALITY | COMPLETENESS | CORE DATA PRT REPRESENTATIVITY | DYNAMIC DATA COVERAGE |
| DATA SCENARIO | 3 | H | H | MODERN | ALL | H |
| | 2 | M | M | MIXED | PARTIAL | M |
| | 1 | L | L | VINTAGE | NONE | L |

DS 1

| | | LOGGING SURVEYS | | | | |
|---|---|---|---|---|---|---|
| | | WELL DENSITY | LOG DATA QUALITY | COMPLETENESS | CORE DATA PRT REPRESENTATIVITY | DYNAMIC DATA COVERAGE |
| DATA SCENARIO | 3 | H | H | MODERN | ALL | H |
| | 2 | M | M | MIXED | PARTIAL | M |
| | 1 | L | L | VINTAGE | NONE | L |

FIG. 4

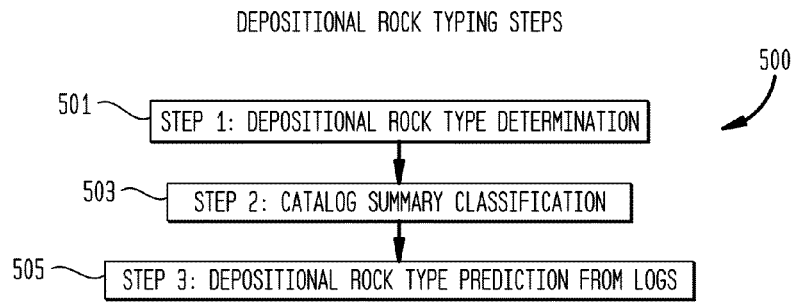
FIG. 5
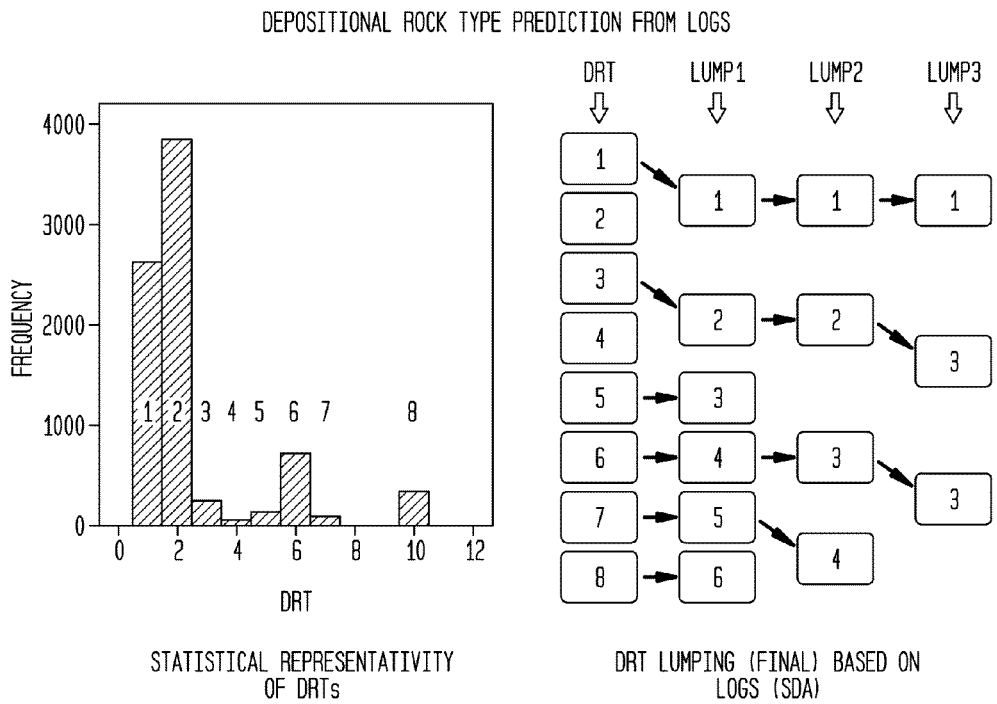
FIG. 6(a)
FIG. 6(b)

DYNAMIC VALIDATION OF PRTs - 3 STEP PROCESS

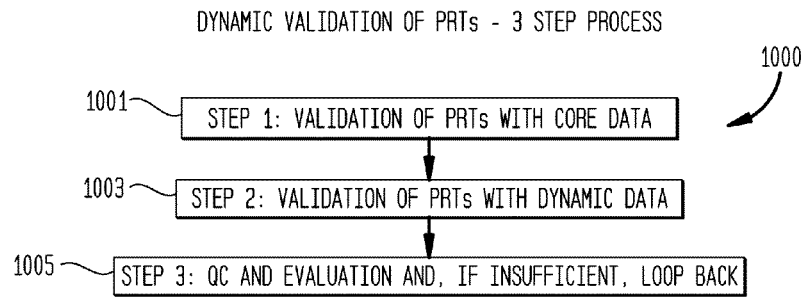

1001 — STEP 1: VALIDATION OF PRTs WITH CORE DATA

1003 — STEP 2: VALIDATION OF PRTs WITH DYNAMIC DATA

1005 — STEP 3: QC AND EVALUATION AND, IF INSUFFICIENT, LOOP BACK

FIG. 14

PRT DISTRIBUTION IN A MODEL

| DATA SCENARIO (LOW ↔ HIGH) | RESERVOIR TYPE I | RESERVOIR TYPE II | RESERVOIR TYPE III |
|---|---|---|---|
| REGULAR WELL SPACING CAPTURING SPATIAL HETEROGENEITY; CORE REPRESENTATIVE FOR ROCK TYPES | SPATIAL TRENDS DRIVEN BY DATA | SPATIAL TRENDS DRIVEN BY DATA | SPATIAL TRENDS DRIVEN BY DATA |
| WELL SPACING NOT CAPTURING SPATIAL HETEROGENEITY; CORE NOT REPRESENTATIVE FOR ROCK TYPES | SPATIAL TRENDS DRIVEN BY DATA AND VALIDATED BY OUTCROP ANALOGS | SPATIAL TRENDS DRIVEN BY DATA AND VALIDATED BY CONCEPTUAL DIAGENETIC MODELS AND OUTCROP ANALOGS | SPATIAL TRENDS DRIVEN BY DATA AND VALIDATED BY CONCEPTUAL DIAGENETIC MODELS |
| GREEN FIELD EXPLORATION WITH FEW APPRAISAL WELLS; LITTLE TO NO CORE | SPATIAL TRENDS DRIVEN BY CONCEPTUAL MODELS FROM OUTCROP ANALOGS AND FSM | SPATIAL TRENDS ONLY PARTIALLY EXPLAINED BY DRTs; SPATIAL TRENDS FROM OUTCROP ANALOGS AND CONCEPTUAL MODELS AND RTM | SPATIAL TRENDS DRIVEN BY CONCEPTUAL DIAGENETIC MODELS AND RTM |
|  | PRTs AND FLOW CONTROLLED BY DEPOSITIONAL ROCK TYPES (DRTs) | PRTs AND FLOW LINKED TO BOTH DEPOSITIONAL AND TRUNCATE DIAGENETIC PROCESSES AND TRENDS | PRTs AND FLOW CONTROLLED BY DIAGENESIS MODELS AND TRUNCATE DRT TRENDS |

FIG. 15

INTEGRATED WORKFLOW OR METHOD FOR PETROPHYSICAL ROCK TYPING IN CARBONATES

TECHNICAL FIELD

Various embodiments described herein relate to the field of petrophysical rock type determination, and methods and systems associated therewith.

BACKGROUND

Much of the known reserves of oil and gas around the world are found in carbonate formations. To optimize the production of these reserves, petroleum engineers seek to understand the physical properties of these formations, including their porosity and permeability. For many geologic formations, their physical properties are determined primarily as they are deposited, and modified to some extent by pressure and heat. Therefore it is possible to describe and classify such geologic formations in terms of their depositional environments, with some acknowledgement of subsequent changes to the physical properties.

Carbonates, however, present an unusual challenge in that their properties may be greatly modified, and the rock type changed completely, by a process of diagenesis. In particular, the pore system may be very different from that found in the original depositional environment. Carbonates also exhibit larger pores, so-called secondary porosity, where diagenetic processes create larger scale pores or "vugs". In some carbonates these vugs are connected, and in other carbonates they are not. These additional factors greatly influence the flow of fluids through the geologic formations. If the carbonates have not been modified by diagenesis, the dynamic or flow properties are those of the rocks as deposited and are controlled largely by the pore types related to the initial texture of the rocks. If the carbonates have been modified by diagenetic processes, their dynamic properties are controlled by a combination of primary porosity determined by the pore types, which may differ from that of the originally deposited rocks, and the secondary porosity with its associated pore types.

Incorporation of rock typing in carbonate workflows is dictated by inherent heterogeneity, variation of pore types and significant impact of diagenetic processes. However, existing methods have significant gaps in: (1) incorporating diagenetic processes; (2) accounting for multi-modal pore throat distributions in pore typing; (3) accounting for fractures; (4) integrating dynamic data; (5) accounting for different scales and (6) providing the appropriate geostatistical tools to properly distribute PRTs in the static reservoir model.

Among other things, what is required is a method of rock typing for carbonates that incorporates diagenetic processes, accounts for multi-modal pore throat distribution in pore typing, takes into account the influence of fractures, and integrates dynamic data.

SUMMARY

According to one embodiment, there is provided a workflow or method for petrophysical rock typing of carbonates in an oil or gas reservoir or field including determining a Data Scenario (DS) for the reservoir or field, determining a plurality of Depositional Rock Types (DRTs) for the reservoir or field, each DRT being based upon depositional attributes associated therewith, determining a plurality of diagenetic modifiers (DMs) or primary textures (PMs) associated with the plurality of DRTs, determining a Reservoir Type (RT) corresponding to the plurality of DRTs and associated with the oil or gas reservoir or field, the RT being categorized as one of a Type I RT, a Type II RT, or a Type III RT, the Type I RT being associated with rocks that have not been substantially modified since deposition and where fluid flow therethrough is controlled principally by the depositional attributes thereof, the Type III RT being associated with rocks that have undergone diagenesis since deposition and where fluid flow therethrough is controlled principally by diagenetic properties associated therewith, the Type II RT being associated with rocks that are hybrids of the Type I RT and the Type III RT, determining at least one pore type, and determining on the basis of the plurality of DRTs, the plurality of DMs or PMs, and the at least one pore type, a plurality of Petrophysical Rock Types (PRTs) associated with the RT. PRTs are rocks which are characterized by specific ranges of petrophysical properties, exhibit distinct relationships relevant for flow characterization, are identified by logging surveys, and are linked to geological attributes like primary texture or diagenetic modifications. The PRTs may also be validated with core data and dynamic data and are used to create 3D models using spatial interrelation rules and trends.

Further embodiments are disclosed herein or will become apparent to those skilled in the art after having read and understood the specification and drawings hereof.

BRIEF DESCRIPTION OF THE DRAWINGS

Different aspects of the various embodiments of the invention will become apparent from the following specification, drawings and claims in which:

FIG. 4 shows a matrix used to evaluate and classify data to enable the choice of a Data Scenario for petrophysical rock typing;

FIG. 5 shows a process flow for Depositional Rock Type (DRT) determination and prediction from logs;

FIG. 6 shows "lumping" of DRTs to a smaller set of DRTs;

FIG. 14 shows a process flow for the dynamic validation of PRTs;

FIG. 15 shows the interrelationships between the Data Scenario and the Reservoir Type;

DETAILED DESCRIPTION

Figure 1:
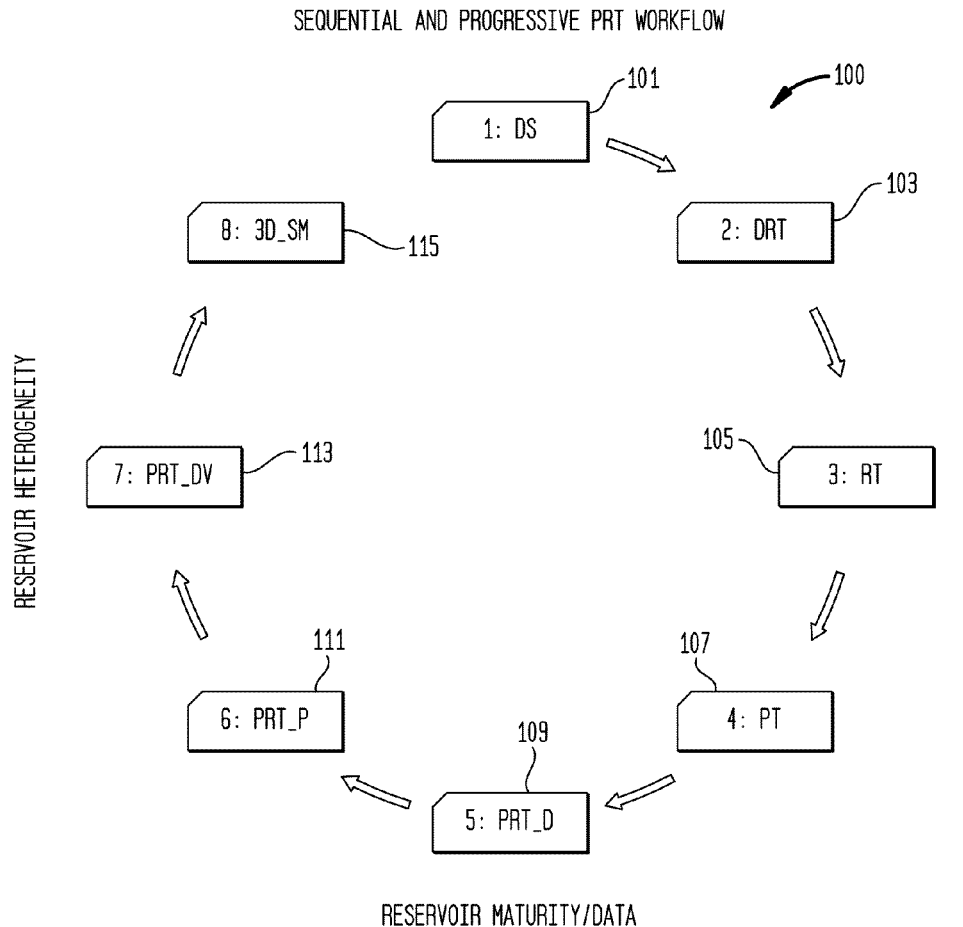
FIG. 1 shows one embodiment of a workflow for petrophysical rock typing in carbonates.

The present invention may be described and implemented in the general context of a system and computer methods to be executed by a computer. Such computer-executable instructions may include programs, routines, objects, components, data structures, and computer software technologies that can be used to perform particular tasks and process abstract data types. Software implementations of the present invention may be coded in different languages for application in a variety of computing platforms and environments. It will be appreciated that the scope and underlying principles of the present invention are not limited to any particular computer software technology.

Moreover, those skilled in the art will appreciate that the present invention may be practiced using any one or combination of hardware and software configurations, including but not limited to a system having single and/or multiple computer processors, hand-held devices, programmable consumer electronics, mini-computers, mainframe computers, and the like. The invention may also be practiced in distributed computing environments where tasks are performed by servers or other processing devices that are linked through a one or more data communications network. In a distributed computing environment, program modules may be located in both local and remote computer storage media including memory storage devices.

Also, an article of manufacture for use with a computer processor, such as a CD, pre-recorded disk or other equivalent devices, may include a computer program storage medium and program means recorded thereon for directing the computer processor to facilitate the implementation and practice of the present invention. Such devices and articles of manufacture also fall within the spirit and scope of the present invention.

Referring now to the drawings, embodiments of the present invention will be described. The invention can be implemented in numerous ways, including for example as a system (including a computer processing system), a method (including a computer implemented method), an apparatus, a computer readable medium, a computer program product, a graphical user interface, a web portal, or a data structure tangibly fixed in a computer readable memory. Several embodiments of the present invention are discussed below. The appended drawings illustrate only typical embodiments of the present invention and therefore are not to be considered limiting of its scope and breadth.

FIG. 1 shows a flow diagram corresponding to one embodiment of workflow 100 for petrophysical rock typing in carbonates. Petrophysical rock typing in carbonate reservoir rocks has long been recognized as presenting an unusual set of challenges. This is partly because carbonates are heterogeneous and their properties can vary over intervals of a few feet, unlike most other rock types. See G. E. Archie, "Classification of Carbonate Reservoir Rocks and Petrophysical Considerations," Bulletin of the American Association of Petroleum Geologists, Vol. 36, No. 2 (February 1952), pp 278-298.

The workflow includes eight composite and sequential steps, which are represented by a loop-type diagram as shown in FIG. 1. Since workflow 100 presented herein describes only the determination and validation of Petrophysical Rock Types (PRT), dynamic simulation is beyond the scope of the present embodiment. The final product of workflow 100 described herein is the result of Step 115, that is, the 3D static model.

At step 101 of workflow 100, the available data are evaluated and the types of data available are determined, which drives the approach to be followed. The starting point for the petrophysical rock typing can be one of several data scenarios. The workflow may include several different types of data. In one embodiment, PRT workflows are designed to be applicable to all Data Scenarios (DS), which are driven by:

(1) well density;
(2) logging surveys (vintage and completeness);
(3) available core data, and
(4) dynamic data.

More is said below regarding this step and the other steps in the workflow.

Still referring FIG. 1, step 103 includes determining Depositional Rock Types (DRT) to test the predictability of unbiased DRTs by logs in order to assess the relative contribution by diagenetic modifiers. At step 105 Reservoir Typing is performed to determine whether the reservoir properties are defined by the Depositional Rock Types or by subsequent diagenetic processes, with consideration also given to the possibility of the flow properties being modified by fracturing. Step 107 includes Pore Typing from core samples and the prediction of Porosity Types from PKS (porosity-permeability-saturation) data and log data.

Still referring to FIG. 1, at step 109 Petrophysical Rock Types are determined according to the relative influence of Depositional Rock Types, Diagenetic Modification (DM), and Pore Types. At step 111 PRTs are predicted across multiple wells. At step 113 the PRTs are validated with core data and dynamic data. Step 115 includes the completion of the spatial interrelation rules and trends for the PRTs extracted in step 111 and results in the static model 3D_SM.

Figure 2:
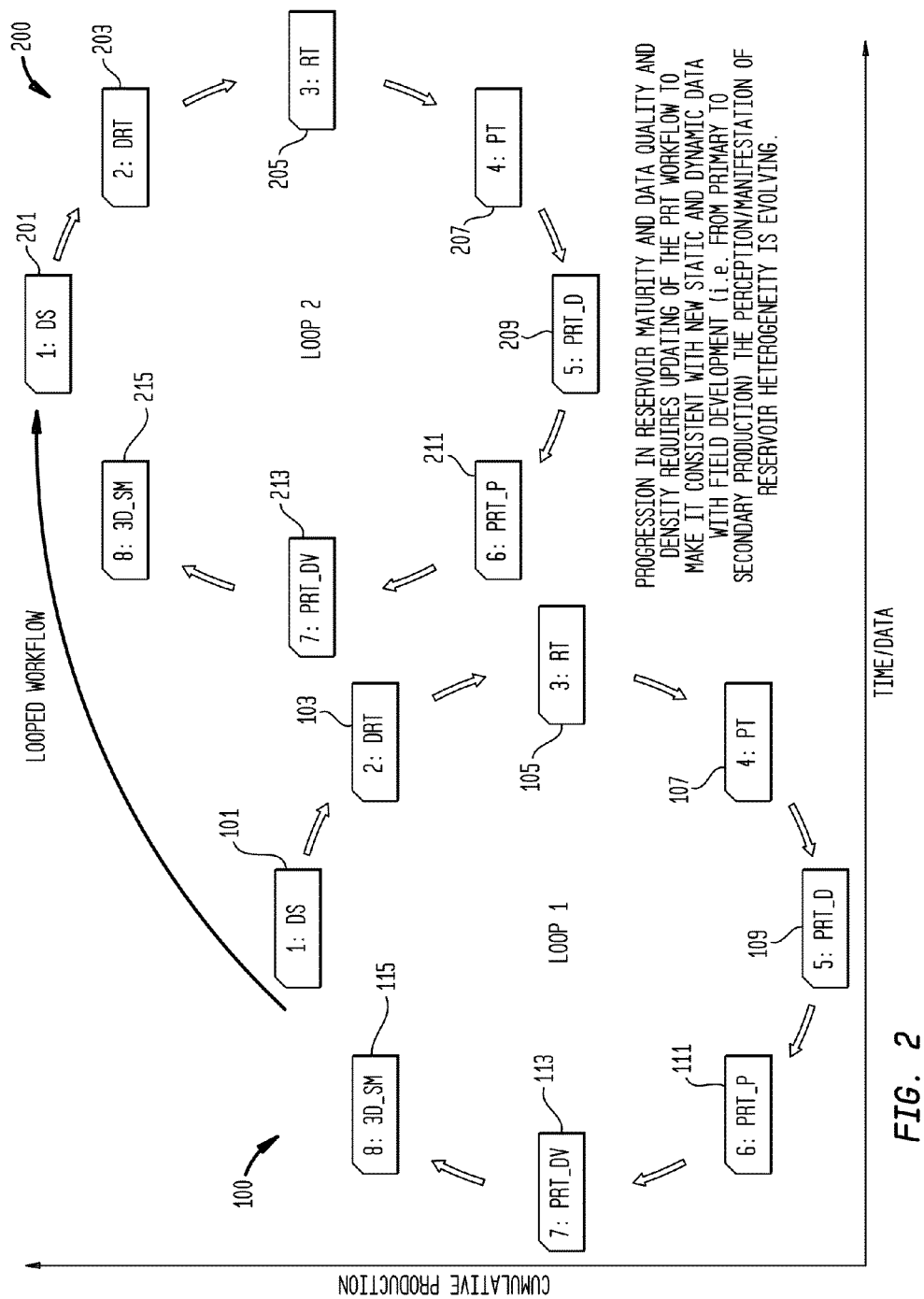
FIG. 2 shows another embodiment of a workflow for petrophysical rock typing in carbonates.

Referring now to FIG. 2, with progressing field maturity and acquisition of new data multiple loops are required to capture reservoir heterogeneity and optimize the representation of the subsurface data. Initial workflow 100 shown in FIG. 1 is replaced by new workflow 200 based in part on results of the previous workflow and in part on the new data acquired as the field is developed. New workflow 200 starts at Step 201 because the first step in the new workflow is to re-evaluate the data and determine the optimal Data Scenario, which may be different from that used in workflow 100. Steps 203, 205, 207 209, 211, 213 and 215 in FIG. 2 correspond to steps 103, 105, 107,109, 111, 113 and 115 respectively in FIG. 1. The process of repeating the loop may be done as often as required as more data become available.

Figure 3:
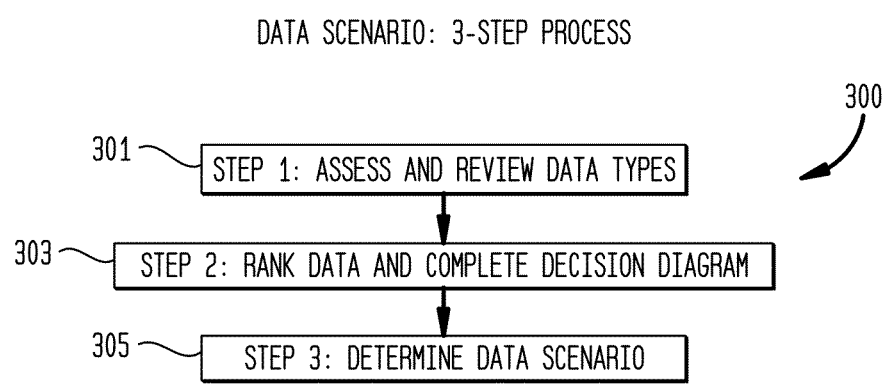
FIG. 3 shows a process flow for determining a Data Scenario for a workflow.

FIG. 3 shows a Data Scenario selection process flow 300 as previously shown in FIG. 1 at step 101 and in FIG. 2 at steps 101 and 201. At step 301 in process flow 300 available data types are assessed and reviewed. The workflow may include several different types of data (MICP, NMR, PKS, etc.), and is not tied to one specific type of data. Some of the factors included in this evaluation may include:

(a) well density within the reservoir or field;
(b) the available well logging survey data, including the types of logs and consideration of their quality, vintage and completeness;
(c) available core data, and
(d) the extent of coverage of flow or dynamic data, such as production logs.

Based on these criteria, the data are ranked at step 303 and the rankings displayed as a decision diagram as shown in FIG. 4. The ranking within the matrix determines which data scenario is used later in the workflow. The data scenario for the workflow is selected in step 305.

FIG. 4 shows a decision diagram or matrix 400 for the Data Scenario definitions. According to some embodiments each type of data is ranked on a three-point scale. The well density (for logged wells), log data quality and dynamic data coverage are ranked as High, Medium or Low. The well logging surveys are ranked for completeness as Vintage, Mixed or Modern. This classification reflects that older well log surveys typically measured only a few reservoir properties, whereas modern log surveys measure many more properties. A ranking of All, Partial or None is then assigned to the Core Data representations depending on the evaluation of to what extent the core data are representative for the petrophysical rock types in the formation defined later in the workflow. Ranking within the matrix influences steps in application of the workflow, as well as subsequent decisions on data acquisition for the next workflow loop.

Data Scenario 1 (DS1) is selected when the well data and log data are sparse and of older vintage, if they exist at all, having little dynamic data and with cores that cannot with confidence be taken as representing the entire field. This scenario may be typical of a newly discovered field where the only available data are from a few exploratory wells and limited core samples.

Data Scenario 2 (DS2) applies when the logged well density is moderate but not extensive, and the log data are of varying quality, with a mix of vintage and modern logs. Such a scenario also has core data from part of the field, but the data are sparse, or unevenly distributed within the field, or cannot be used with confidence to predict the rock types across the field. Such a data scenario may be found for example in an older field where new technology or a change in the economics of production has resulted in renewed drilling and enhanced recoverable reserves.

Data Scenario 3 (DS3) is typical of a mature field where the logged well density is high, there are modern well logs, or a mix of older and modern logs, with medium to high data quality. The modern logs are more complete, with more reservoir properties measured, such that the mix of modern logs with some older logs results in a completeness ranking of mixed to high. The dynamic data coverage can also be categorized as medium to high for the entire field. In Data Scenario 3, the core data are substantially representative, or at least partially representative, of the petrophysical rock types across the entire field.

According to some embodiments it is expected that as a field matures, more data become available and the looping process shown in FIG. 2 is applied, the chosen data scenario will shift towards Data Scenario 3. In some embodiments, the score from this ranking matrix may be used to influence future data collection strategies with the intent of reducing or eliminating gaps in the data, thus moving more rapidly towards Data Scenario 3.

Referring now to FIG. 5, flow 500 shows the steps required for the depositional rock typing step of the workflow, previously shown as step 103 in FIG. 1 and step 203 in FIG. 2. In carbonates, the key to understanding the rock types is an appreciation of both the depositional environment and also of how much the deposited carbonate formations may have been subsequently changed by diagenetic processes. As a result of the diagenesis, the porosity of the rocks may be very complex, requiring a description not only of the primary porosity of the rocks, but also consideration of the secondary porosity, vugs and fractures. To meet this need, several classification schemes for carbonates have been proposed and used within the industry. For one classification scheme, see Choquette et al., "Geologic Nomenclature and Classification of Porosity in Sedimentary Carbonates," Bulletin of the American Association of Petroleum Geologists, Vol. 54, No. 2 (February 1970), pp 207-250. For a further classification scheme, see Robert J, Dunham, "Classification of Carbonate Rocks According to Depositional Texture," 1962. For an expanded version of Dunham's classification, see Embry et al., "A Late Devonian Reef Tract on Northeastern Banks Island, N.W.T.," Bulletin of Canadian Petroleum Geology, Vol. 19, No. 4 (December 1971) pp 730-761.

A somewhat different approach to classifying carbonates, based on visual examination of pore space, is described by F. J. Lucia, "Petrophysical Parameters Estimated from Visual Descriptions of Carbonate Rocks: A Field Classification of Carbonate Pore Space," Society of Petroleum Engineers Annual Conference, October 1981, pp. 629-637. The Lucia classification is frequently used and referenced in other papers on carbonate classification. For an expanded version of this classification scheme, with illustrations of various pore types, see Lucia et al., "Predicting Permeability From Well Logs in Carbonates with a Link to Geology for Interwell Permeability Mapping," Society of Petroleum Engineers, Reservoir Evaluation and Engineering, August 2003, pp 215-225. An alternate classification scheme was proposed by Marzouk et al. in "New Classification of Carbonate Rocks for Reservoir Characterization," of Petroleum Engineers SPE #49475, 8th Abu Dhabi International Petroleum Conference, October 1998.

At step 501, an "unbiased" determination is made of the depositional rock types from core data. An "unbiased" determination is one in which the depositional rock types are assigned based solely on depositional attributes without attempting to factor in changes that may have taken place after deposition as a result of diagenesis or other processes. Some of the depositional attributes considered include texture, mineralogy, dominant fossils, sedimentary features, character of bedding contacts, and environment of deposition (EoD) as a function of depth along the cored intervals. A geologist usually makes this determination. The difference between this approach and conventional approaches to DRT determination is that there is a strict requirement to identify the rock types as deposited, not necessarily as they appear now in core samples after diagenetic modification.

During the DRT determination, any indicators of diagenetic modification are described as a separate data set. Such indicators of diagenetic modification may include dolomite or calcite crystal size, the presence of dispersed clay, the presence of anhydrite nodules or bitumen, the abundance of cement or certain dominant pore types. In some embodiments the attributes are represented using a system of numeric codes in a spreadsheet format. It is usual in PRT workflows to either assess the effects of diagenetic activity at a later stage, or to incorporate some allowance for diagenetic effects at this early stage. Often the rock type is described as it appears in the sample, without regard to the distinction between the Depositional Rock Type and the current Petrophysical Rock Type. In the workflow described here, the effects of the diagenetic activity are noted but not included at this stage. It is important that diagenetic modification be integrated into the workflow at an early stage. Typically carbonate formations are analyzed by mapping the depositional rock type and then later making allowances for diagenetic modifications. The diagenetic modifications have such a large impact on the rock type and the pore system that they should be integrated as early in the analysis as possible, which is what the present method does.

One result of this process is a set of Depositional Rock Types (DRTs) that represent categories of non-overlapping lithofacies. The number of Depositional Rock Types may be defined by the geologist. Another result of this process is a separate set of diagenetic attributes. These attributes may be used later in the workflow to explain the discrepancies between the observed reservoir properties and the DRTs. As explained previously, such discrepancies are caused by the action of the diagenetic modifiers on the carbonate formations.

Still referring to FIG. 5, the DRT catalog is created at step 503. This represents the DRT elements of a depositional model based on core observations and concepts from literature and/or analogs. The DRT catalog includes one or more alternate scenarios that combine DRTs according to geological criteria such as depositional regions, facies belts, etc., to a statistically acceptable number for prediction using logs, generally no more than 15 combined DRT categories. The Depositional Rock Type Catalog also provides a reference set of Depositional Rock Types that includes all the known Depositional Rock Types within the reservoir.

Still referring to FIG. 5, at step 505 the Depositional Rock Types are predicted across the reservoir using well log data. Typically this process is performed by a petrophysicist. Prediction of DRTs from logs requires "lumping" and "splitting" of the DRTs determined from core. The lumping/splitting scheme is guided by two factors: (1) statistical representations of the DRTs and, (2) distinct differences in physical and log space. Data points with lower statistical significance are "lumped" or merged with other data points of higher statistical significance that are similar geologically. Lumping/splitting should follow geological (DRT) associations, and generally follows the DRT groupings already made in the DRT catalog. Prediction of DRTs from logs is generally performed using multivariate statistical tools such as Step-wise Discriminant Analysis (SDA) or neural networks combined with deterministic methods. The result of step 505 is the generation of DRT_pred values.

FIG. 6(a) shows an example of the statistical representations of a data set, and FIG. 6(b) shows the eight resulting DRTs (and/or groupings) based on geological descriptions. The statistical representations along with the geological groupings from the DRT catalog are used to determine further lumping and increase predictability to an acceptable degree resulting in DRT association "Lump3" as shown in FIG. 6(b), in which the number of distinct DRTs has been reduced to three.

Figure 7:
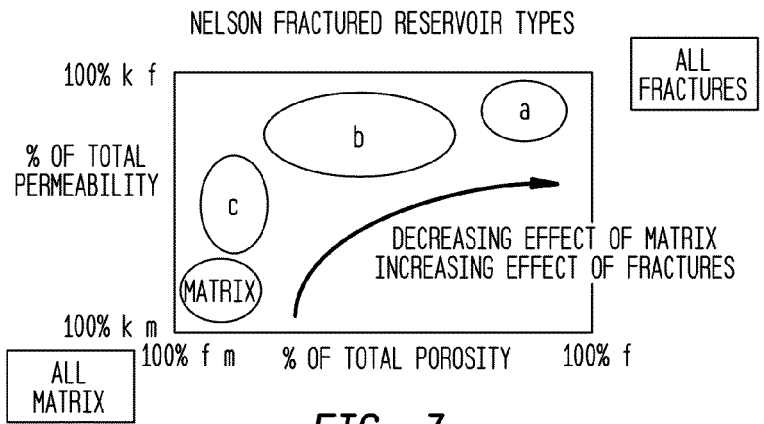
FIG. 7 shows Nelson fractured reservoir type classification.

FIG. 7 shows a plot of porosity vs. permeability for fractured Reservoir Types, illustrating Nelson fracture types. See Nelson, R. A. "Geologic Analysis of Naturally Fractured Reservoirs," 2nd ed. (2001), Gulf Publishing, Houston. Carbonate reservoirs are highly susceptible to diagenetic processes, which alter their original depositional order and petrophysical properties. Diagenesis may radically change the properties of the rocks. Different fluids at different depths produce different changes in the carbonates. Understanding these changes to the properties of the rocks is critical in determining the petrophysical rock types, but unlike the proposed method, is usually not included in the analysis at this stage. In addition, fractures can overprint systems that are dominated by depositional processes and also those that are modified by a diagenetic overprint. Since relatively little is known of the processes and spatial distribution of fractures, the Nelson fracture types are a reliable classification of the influence of fractures on the dynamic properties of carbonate reservoirs. Nelson fracture types were defined on their relative contribution to permeability and porosity and range from "a" to "b" and "c" where "a" defines dominant fracture control, while "c" represents dominant matrix control on flow.

Figure 8:
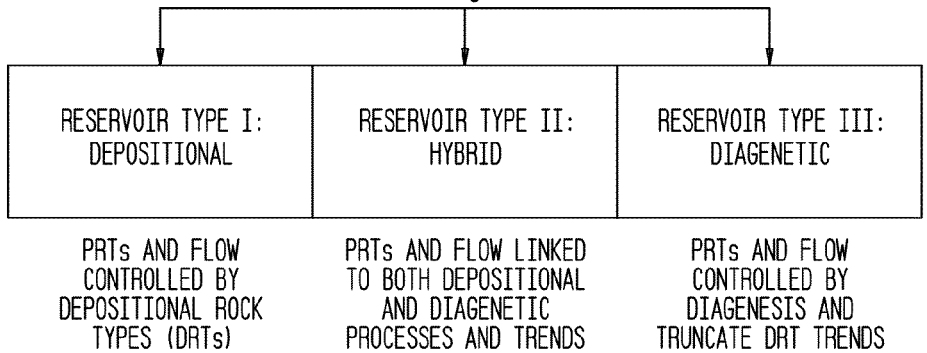
FIG. 8 shows three Reservoir Types ranging from Depositional to Diagenetic.

FIG. 8 shows a decision tree for the process of Reservoir Typing (RT). Reservoir Typing is the determination of the relative contribution on fluid flow of the degree of Diagenetic Modification (DM) of the original depositional rock types (DRTs) and, when present, the Nelson fracture types. A cumulative DM is the result of one or more diagenetic events (or modifiers) that have impacted the rock at different times with varying conditions of permeability and porosity, temperature, pressure and fluid composition. Conventional workflows assume that the rock properties are controlled primarily by the depositional rock types and then apply "fudge factors" later to account for diagenesis. The proposed workflow allows for the possibility that the rock properties have been altered by diagenesis.

Where no fractures are observed to influence flow, the RT index takes one of three possible values:

when DM is negligible or conforms to the DRTs, flow is principally controlled by depositional rock types, and therefore the RT equals Type I (which is a Depositional Reservoir Type);

when DM overprints and crosscuts the DRTs, flow is principally controlled by diagenetic modification, and therefore the RT equals Type III (which is a Diagenetic Reservoir Type) and when flow is linked to both depositional rock types and diagenetic processes and trends, and therefore the RT equals Type II (which is a Hybrid Reservoir Type.)

In the workflow, a three-step process may be used to determine Reservoir Type. This process is used to determine if there is a correlation between the DRT and the flow properties of the reservoir. If there is, then DRTs control the flow and the Reservoir Type is Type I. If the process shows little or no correlation between DRT and flow, then the Reservoir Type has been changed since deposition and the cumulative effect of the diagenetic modifiers (the resulting DM) control the flow, such that the Reservoir Type must be Type III or Type II.

For Type I reservoirs, the Petrophysical Rock Types are described by the DRTs. That is, the rocks are substantially what was deposited and their flow properties have not been changed by subsequent processes. For Type III reservoirs, diagenesis has changed the properties of the carbonates, and changed the flow properties, such that the flow properties are controlled principally by the end results of the diagenesis and have no relationship to the properties of the antecedent deposited rocks. The Petrophysical Rock Type is no longer the same as the Depositional Rock Type. A Type II reservoir is a hybrid, and flow is controlled by a combination of deposition and diagenetic properties.

When fractures contribute to flow, the three possible Nelson fracture types are indicated by adding "a," "b" or "c" to the primary Reservoir Type.

Figure 9:
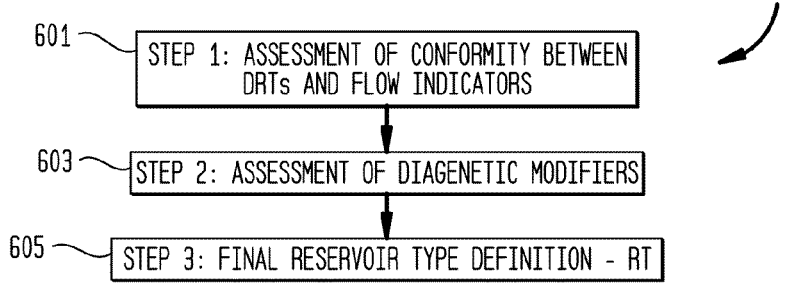
FIG. 9 shows a process flow for Reservoir Typing.

Referring now to FIG. 9, three-step process 600 is used to complete the Reservoir Typing. This process corresponds to Step 105 in FIG. 1. Step 601 is the Assessment of Conformity between DRTs and Flow Indicators. The recommended indicators for a quantitative assessment of conformity between DRTs and flow indicators are:

(1) comparing DRTs with PKS data such as porosity-permeability cross plots and Lorenz plots, and (2) comparing DRTs with dynamic data, such as well production logs (PLTs), drill stem test data (DSTs) and wire line formation test (WFT) data.

If the result is a high degree of conformity between DRTs and flow indicators, the RT as described above is classified as RT 1 and step 603 can be skipped. In this case, present baffles or barriers are identified or confirmed as DRTs. If there is no conformity the fluid flow is controlled, at least in part, by the diagenetic modifiers and the following step is needed.

Step 603 includes assessing the effects of the diagenetic modifiers. This assessment may use core data and descriptions of diagenetic attributes. Such descriptions can be created in parallel with DRT descriptions at 601 or introduced at this stage. The additional core analyses may include petrographic analysis, Mercury Injection Capillary Pressure (MICP), Scanning Electron Microscopy (SEM), cathodoluminescence (CL), geochemistry, etc., which can be used for the identification of diagenetic modifiers. Other techniques will become apparent to those skilled in the art after having read and understood the specification and drawings hereof.

The effects of the Diagenetic Modification on secondary porosity indicators such as fractures and vugs can be identified from logs, including image logs, such as formation microscanner imager or nuclear magnetic resonance logs and drilling data, such as fluid losses, rate of penetration, etc. The result of this step is an assessment of the type and degree of diagenetic modifiers, which should be included in the PRT definition of Step 109 and classification of the RT. The comparison of diagenetic modifiers with dynamic data establishes their contribution to flow or barriers. Where there is significant fracture development, the RT is a separate category and requires a different approach for petrophysical evaluation and modeling that is not covered by the rock typing workflow and is therefore not discussed here.

Still referring to FIG. 9, the Final Reservoir Type is determined at Step 605 based on the relative contribution of DM and fractures on flow.

Figure 10:
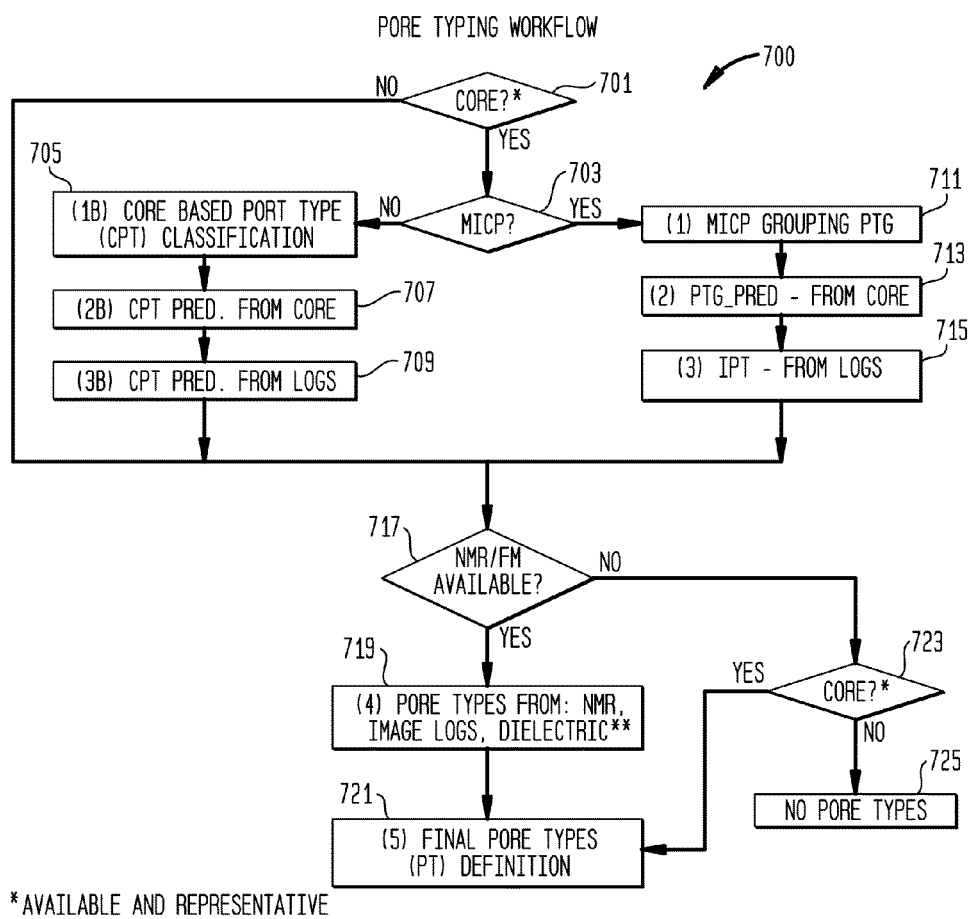
FIG. 10 shows a workflow for Pore Typing, depending on the availability of certain data.

FIG. 10 shows Pore Typing workflow 700. This workflow corresponds to Step 107 in FIG. 1. Carbonate petrophysical heterogeneity (flow properties) is generally the result of complex and multi-modal pore systems including fractures. Identification and prediction of pore types is therefore essential for a reliable rock typing in carbonate. Pore typing and a general understanding of the porosity characteristics are critical to understanding the porosity and permeability of a reservoir. See Amaefule et al, "Enhanced Reservoir Description: Using Core and Log Data to Identify Hydraulic (Flow) Units and Predict Permeability in Uncored Intervals/Wells," Society of Petroleum Engineers, SPE 26436, 68th Annual Technical Conference, Houston, Tex., October 1993. For a further discussion of porosity and pore types, see Arve Lonoy, "Making sense of carbonate pore systems," AAPG Bulletin, v. 90, no. 9 (September 2006), pp. 1381-1405. For a further discussion in which MICP testing is used to assist with pore typing and pore throat distribution analysis, see Clerke et al., "Multiple Discrete Pore Systems in Arab D Limestone," from oral presentation at AAPG Annual Convention, San Antonio, Tex., Apr. 20-23, 2008.

In some approaches to petrophysical rock typing, pore or pore throat size are included. However, the usual approach is to take pore type data from subsamples of whole cores or cuttings. The pore throat size is estimated using techniques such as MICP. However, these values are generally from subsamples and of small volume. Further, they tend to show the primary porosity, which is on the micro- to nanometer scale. Determining the secondary porosity, which is on the millimeter to meter scale is possible for the whole core samples, but may be different within a short distance, perhaps within a few meters, of the sample. Therefore upscaling the porosity values to cover a larger area, such as the volume encompassed by a series of wells, is not easily done and often has involved considerable guesswork. One solution to the problem is to integrate well log data into the Pore Typing process.

The Pore Typing workflow is based upon different data scenarios depending on availability of core, MICP data and specialty logs data such as NMR or Formation Microscanner (FM). For a discussion of the use of NMR in pore typing, see Ramakrishnan et al., "A Model-Based Interpretation Methodology for Evaluating Carbonate Reservoirs," Society of Petroleum Engineers, SPE #71704, SPE Annual Technical Conference and Exhibition, New Orleans September 2001.

In workflow 700, decision step 701 asks whether or not cores are available. If cores are available, the flow proceeds to 703, MICP availability. If MICP data are available, the MICP testing process provides comprehensive data to characterize the pore system, linked to its dynamic performance through its pore throat size distribution. MICP derived pore types (IPT) have to be combined with larger scale observations such as vugs and fractures. This information is provided by specialty logs. The next step is MICP/Digital Core Data Grouping step 711. Clustering data from the full range of capillary pressure provides a way to include full scale of porosity from nanopores to macropores and account for multimodal systems. MICP grouping can be done using statistical clustering techniques or neural networks. The resulting groups are named Pore Type Groups (PTGs). PTGs can be also obtained from Digital Core 3D data with appropriate integration of multi-scale volumes.

Still referring to FIG. 10, the MICP branch of the workflow then moves to Prediction of PTG from core PKS Data 713. PTGs are defined only for MICP or Digital Core samples, which usually have a limited number of samples. The ability to make a reliable prediction of PTGs from PKS data can increase the pore type database by an order of magnitude. Prediction of PTGs from core PKS data can be done by multivariate statistical methods such as Stepwise Discriminant Analysis (SDA) or neural networks. Typical predictive variables are Winland parameter R35, log K, PHIE (effective porosity) and sqrt(k/phie). The resulting PTG_pred is used to define PTG predictive algorithms using well logs.

Pore type groups are then also predicted from logs at 715. A robust population of PTG_pred can be integrated with log data to design the prediction of pore types from logs. Previously computed values of PTG_pred are integrated with log data to expand the extent of the available Pore Type data. It is recommended to use all available logs including raw measurements, interpreted logs (effective porosity, mineral volumes etc.) and transformed logs (logarithmic, SQRT, inverse transforms) as an input to SDA to define the optimal combination of predictive logs. Prediction can be performed using either Step-wise Discriminant Analysis (SDA) or neural networks. The product of PTG predicted from logs is referred to as Initial Pore Type (IPT).

Where no MICP data are available, but cores are available, the flow branches to 705 where the alternate path is to use Core Based Pore Type Classification (CPT). CPT classification is based on core descriptions and thin sections classifications of the pore system leading to definition of Core Pore Types (CPTs). CPTs are then subject to prediction, using the methods described above, from conventional core data at 707 and logs at 709 yielding CPT_pred values.

Still referring to FIG. 10, in the event that no core is available (and therefore no possibility of obtaining MICP data) the only remaining option is to look for NMR or FM log data as shown at decision point 717. Decision point 717 is also the next step in the flow when cores are available, with or without MICP data.

Pore Type Groups are defined from samples of limited volume and might miss pore types of larger scale such as fractures and vugs. To complement information from a larger scale porosity, specialty log data such as Formation Microscanner (FM), Nuclear Magnetic Resonance (NMR) and acoustic data are used at 719 to compute pore types. Fractures are defined from FM and complemented with Stoneley waves, PLT and drilling data for defining effective fractures. Vugs are defined from FM (>3 mm) or NMR (<0.1 mm) and validated and integrated with core images or pore scale modeling based on Computer Tomography (CT) scans when available. Determination of secondary porosity can be performed using NMR, FM or any combination of specialty logs.

If no suitable logs are available at 717, and no cores at 723, then the process terminates at 725 without being able to determine pore type. In the event that core data are available, but no logs, the flow moves on to Final Pore Type Definition—PT at 721. At this point IPT from 715 or CPT_pred from 709 are combined with the secondary porosity assessment from 719 to define Pore Types. The definition should include only predominant pore types, which can be predicted from logs in a consistent manner throughout the field. Where there are no NMR and/or FM data, pore types (PT) may be defined from IPT from 715 (when MICP data are available) or CPT_pred from 709.

Still referring to FIG. 10, at 721 IPT from 715 or CPT_pred from 709 are combined with the secondary porosity assessment from 719 to define Pore Types. The definition should include only predominant Pore Types, which can be predicted from logs in a consistent manner throughout the field.

Figure 11:
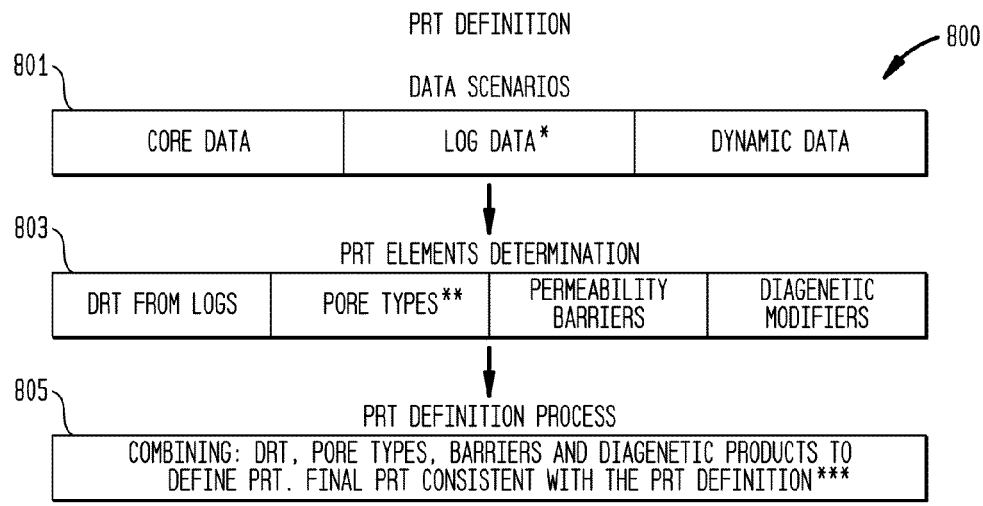
FIG. 11 shows an overview of a data flow for the petrophysical rock type (PRT) definition process.

Referring now to FIG. 11, step 800 in the workflow is the Petrophysical Rock Type (PRT) Definition. This corresponds to Step 109 in FIG. 1. There are no standardized industry-wide definitions for PRT. It is possible to input log properties into a model, but then the question is how to link them to geology. There is a need to be able to distribute petrophysical rock properties spatially, using the logs and knowledge of the spatial variation of the depositional and diagenetic processes that control those properties. One approach sometimes used in the industry is known as electrofacies, that is, "the set of well-log responses that characterize a lithologic unit and permit that stratigraphic interval to be correlated with, or distinguished from, others". (SEG Dictionary of Geophysics). But this is log typing, not rock typing, and lacks a good relationship to the geology.

In the context of this workflow, PRTs are defined as the category of rocks which:
- are characterized by specific ranges of petrophysical properties;
- exhibit distinct relationships relevant for flow characterization;
- are identified by logging surveys and
- are linked to geological attributes like primary texture or diagenetic modifications.

See Skalinski et al., "Rock Type Definition and Pore Type Classification of a Carbonate Platform, Tengiz Field, Republic of Kazakhstan," SPWLA 50th Annual Logging Symposium, June 2009.

In the proposed method, the previously chosen Data Scenario is used at 801. The Data Scenario was chosen based on the availability of core data, log data and dynamic data, the elements needed for the PRT determination at 803. At 805 PRTs are defined according to the relative influence of the following attributes: permeability barriers, DRTs, DM, and Pore Types. The permeability barrier(s) are either non-reservoir rocks or low-permeability rocks that act as flow barriers or baffles indicated by dynamic data. The following conceptual equation describes the relationship between DRTs, DM, PRTs and RT. If there is no apparent diagenetic modification of the flow properties, then set DM=0. If the flow properties have been heavily modified by the diagenetic processes, then set DM=1. Where the flow properties of the deposited rocks have been partially modified by diagenesis, then DM is assigned a value between 0 and 1, then:

if DM~0, then PRT~DRT and RT=I;
if DM~1, then PRT~DM, DRT~negligible, and RT=III, or
if DM does not approximate 0 and if DM does not approximate 1, i.e. DM is neither high nor low, then PRT is a hybrid of DRT and DM, and RT=II.

In summary, PRTs are defined by combining PRT elements such as: DRT_pred, PT, barriers, and other diagenetic modifiers affecting the log response. The foregoing PRT definition includes the primary criteria used to define PRTs from PRT elements. Final PRTs should conform to all 4 segments of the definition. Typical petrophysical rock typing workflows do not include the diagenetic modification this early in the flow, but rather rely on depositional rock typing for much of the analysis with some compensation for diagenetic effects near the end of the flow. Introducing the diagenetic modification into the definition of the PRTs at this point results in a more accurate PRT model and a much closer fit to the dynamic data.

Figure 12:
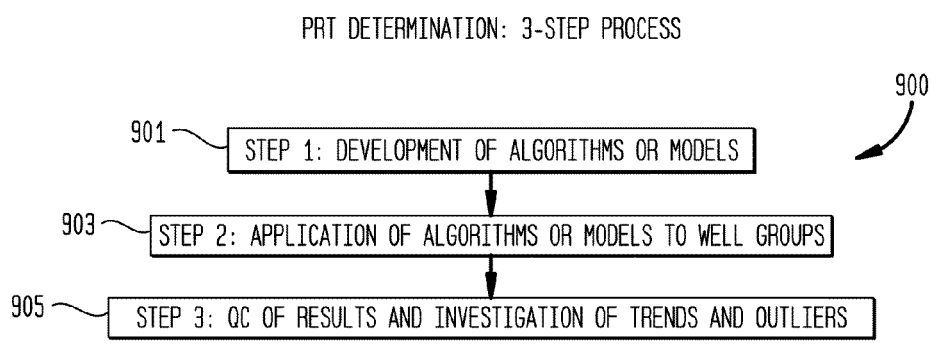
FIG. 12 shows a process flow for Petrophysical Rock Type (PRT) determination.

FIG. 12 shows PRT Determination in a multi-well setting and QC using maps, as shown in flow chart 900. This corresponds to Step 111 in FIG. 1, and includes the determination of PRTs in all wells using predictive algorithms developed in the previous steps. The resulting well data are mapped across the field and investigated for outliers and possible underlying reasons. Next, spatial trends and relationships between PRTs are extracted. This step is especially critical when RT is higher than 1 and the flow is dominated by diagenetic modification. Step 901 of this part of the workflow includes Development of Algorithms or Models for PRT Prediction. In this step all prediction algorithms and/or models defined for prediction of DRTs, pore types and barriers are combined to develop a program to calculate PRTs from log data. The program accounts for different logging data scenarios as discussed previously.

In step 903 programs developed in step 901 are applied to all wells to calculate continuous PRT logs. PRT values are assigned to each logging depth frame and can take only integer values. Different program alternatives corresponding to different logging scenarios can be applied to adequate well groups (for example old vintage logs vs. modern logs). This section of the workflow is completed by step 905 in which calculated PRTs are analyzed using simple maps to identify trends and outliers. Close cooperation between the petrophysicist and the geologist is needed to assure proper analysis and validate and/or explain observed trends. Outliers can result from bad logs, unaccounted rock type or sparse data, and should be explained, corrected or discarded.

Figure 13:
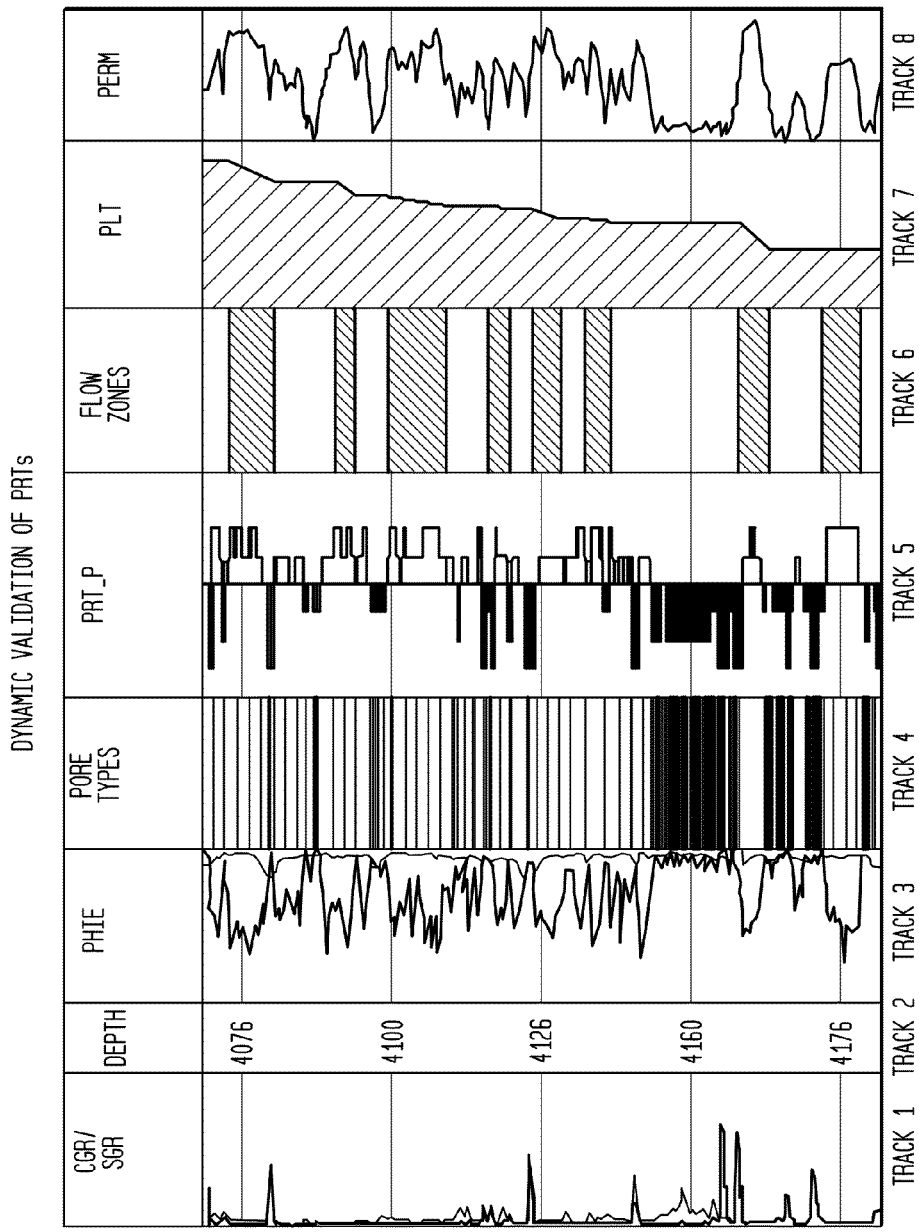
FIG. 13 shows dynamic validation of PRTs with core data.

FIG. 13 shows an example of data from a well. The integration of PRTs with dynamic data such as production logs (PLT), pressure profiles from formation testers or transient pressure test results can help validation of PRTs in terms of their conformance with flow units and barriers. FIG. 13 illustrates this step and contains:
  track 1—spectral GR;
  track 2—depth;
  track 3—log and core porosity;
  track 4—pore types;
  track 5—PRT predicted;
  track 6—flow zones from PLT;
  track 7—PLT profile;
  track 8—permeability from logs and PLT.

As seen in FIG. 13, permeability barriers correspond to microporosity (defined in this example as pore throat radius <0.3 microns) and PRTs 1-3 (black shading on PRT track)

while flow units correspond to PRTs 4-6 (no shading). PRTs are validated since PRTs corresponding to poor or no reservoir (PRTs 1-3 and pore types 1-2) are aligned with no flow zones with low permeability, while PRTs corresponding to the best reservoir (PRTs 4-6) are aligned with flow zones defined from PLT.

To achieve the results shown in FIG. 13, it is necessary to validate the PRTs against dynamic data. The dynamic data may be obtained from well data or from core sample flow tests. For a discussion of the relationships between flow data, pore types and petrophysical rock types, see Gunter et al., "Early Determination of Reservoir Flow Unites Using an Integrated Petrophysical Method," SPE #38679, Society of Petroleum Engineers Annual Conference, October 1997.

A quantitative validation of the link between PRTs and flow indicators may be achieved by (1) comparing PRT with PKS data (such as porosity-permeability cross plots and Lorenz plots) and (2) the comparison of PRTs with dynamic data such as Production Logs (PLTs), drill stem test data (DSTs) and wire line formation test (WFT) data. The goal of this step is to confirm that PRTs are linked to flow profiles observed in dynamic data. In particular barriers and flow zones should be correlated to appropriate PRTs. If the linkage is poor, a look-back to the step 109 of FIG. 1 is required.

Referring now to FIG. 14, in step 1001 of data flow 1000, the PRTs are validated with core data. Data flow 1000 corresponds to step 113 in FIG. 1, and is where the workflow begins to complete the loop, as the PRT data are linked back to the flow data. The dynamic data (flow data) are often omitted from conventional PRT workflows. This may be because the data are not available, or because no good way has been developed to integrate this type of data into the PRT process. The proposed method overcomes this limitation by assigning the correct PRTs including diagenetic modification before comparing the expected flow data with the actual flow data. Earlier in the process, DRT values were compared to the flow data to verify if the flow was controlled by the depositional setting and attributes. Now the flow data are linked to the PRT data, and if the correct rock types have been assigned, including the diagenetic effects, there will be a correlation here even if there was no correlation between the DRT and the flow data.

Cross-plotting core porosity vs. core permeability with PRTs as a filter can reveal the potential impact of rock types on reservoir performance and conformance with the PRT definition. The creation of Lorentz plots using core data and PRTs helps validation in terms of potential flow units. This step requires a representative amount of core samples with adequate population of all PRTs, which can typically be achieved only with core data from more than one well.

In step 1003 of data flow 1000 the PRTs are validated with dynamic data. The integration of PRTs with dynamic data such as PLT, pressure profiles from formation testers or transient pressure test results can help validation of PRTs in terms of their conformance with flow units and barriers. The results are shown in FIG. 13.

Still referring to FIG. 14, the final step 1005 of data flow 1000 is to perform a PRT Conformance Assessment. If PRT conforms to core and dynamic data, then the workflow continues with the next workflow step, otherwise it loops back to step 109 of FIG. 1. In the case where no data are available, or the available dynamic data are sparse, this step can be skipped.

FIG. 15 shows a table of the interrelationships between a PRT distribution method, Data Scenario and the Reservoir Type. This table is created during PRT Distribution and Spatial Validation. At step 113 in FIG. 1 PRT values are extracted.

Step 115 in FIG. 1 represents completion of the spatial interrelation rules and trends for PRTs extracted in step 111 in FIG. 1. Those rules and trends may be used as soft constraints (probability maps) and in designing training images or variograms for the distribution of PRTs in 3D models. The distribution method is also a function of RT and the selected data scenario as described in FIG. 15. In other words, spatial patterns of, and interrelationships between, PRTs are controlled by the relative contribution of depositional versus diagenetic processes (as shown in FIG. 8). In the case where RT equals I, PRTs and flow are controlled by DRTs. In addition to RT, the data density also controls the choice of methods to distribute PRTs in the static model. With increasing density of data, the spatial trends are driven by well control rather than by concepts. Multiple Point Statistics (MPS) is suggested as the best geostatistical tool to honor trends of—and spatial interrelationships among—PRTs.

Figure 16:
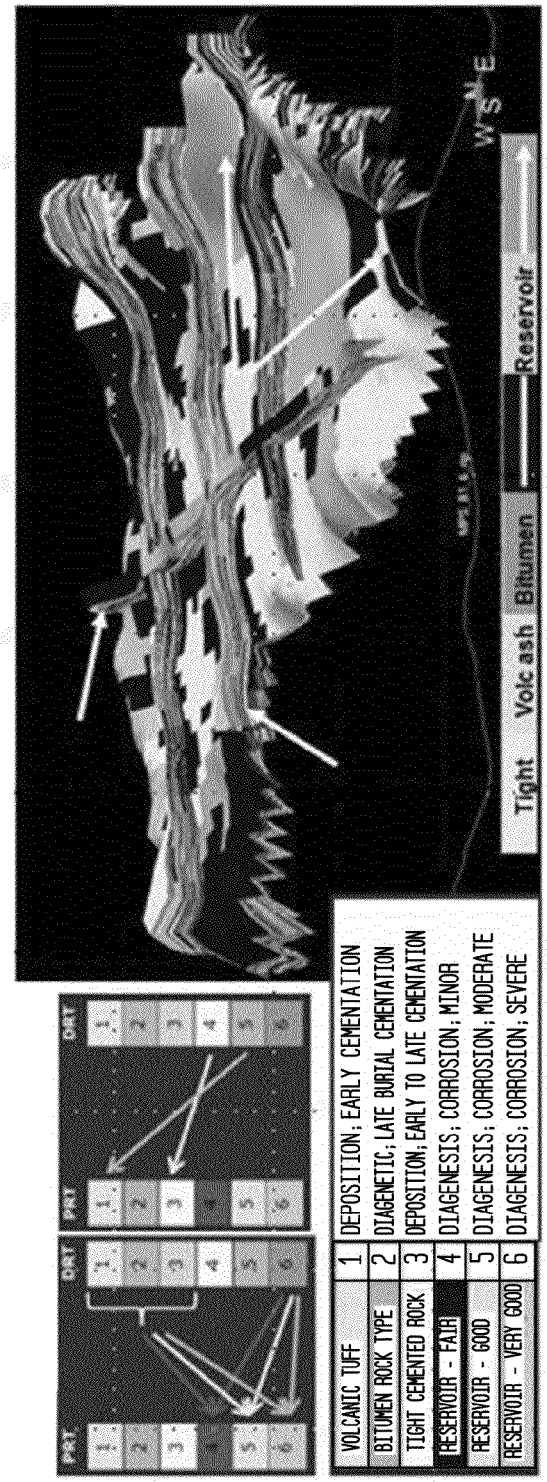
FIG. 16 shows an example of PRT definition and distribution using Multiple Point Statistics (MPS)

FIG. 16 shows an example of PRT definition and distribution using MPS. High resolution and quality 3D seismic data can be used as soft constraint for PRTs, especially for green fields or intermediate fields where well density is not capturing spatial heterogeneity.

Figure 17:
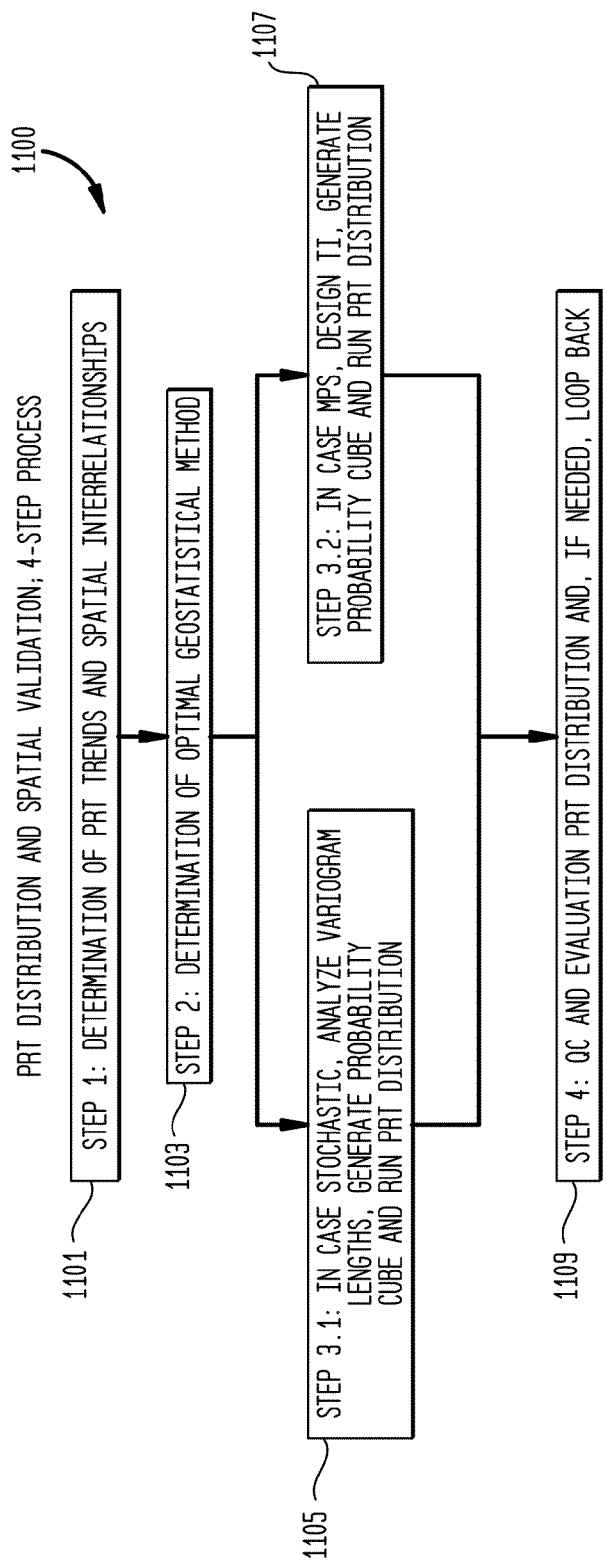
FIG. 17 shows a work flow to accomplish the PRT distribution and spatial validation process.

FIG. 17 shows workflow 1100 including five steps to accomplish the PRT Distribution and Spatial Validation process. Workflow 1100 corresponds to Step 115 in FIG. 1. Step 1101 includes the Determination of PRT Trends and Spatial Interrelationships. This step includes the completion of the spatial interrelation rules and trends for PRTs extracted by mapping PRTs determined in all wells across the field, and investigating for outliers and underlying causes and supplementing information on the spatial interactions and relative proportions from core, analogs, conceptual models and literature. It is assumed that the sequence stratigraphic framework was designed and located in a geocellular model (such as an sgrid) during step 103 of workflow 100.

PRT can be modeled using a wide variety of geostatstical techniques; the optimum technique depends on data density and the nature of the reservoir studied. Step 1103 achieves the Determination of the Optimal Geostatistical Method. These methods include, but are not limited to, variogram-based geostatistics and pattern based or multi-point statistics. Variogram-based geostatistics are mathematically simplistic (2-point statistics). Variogram-based techniques are pixel-based and are founded on the assumption of that a population in a certain region or zone is stationary. The correlation variogram describes the dissimilarity between variables at two spatial locations and its value is calculated by combining information at similar lag distances together in a single bivariate scatter diagram. In general, variogram-based geostatistics are too limiting in capturing realistic geological heterogeneity observed in analogs from outcrops and conceptual models (i.e., Caers and Zhang, 2002; Caers, 2007; Strebelle and Levy, 2008). However, when data density is capturing geological heterogeneity (i.e., mature field with high well density) or in cases where the geological heterogeneity is unknown (too little data or poorly constrained spatial relationships between PRTs) variogram-based methods may very well be sufficient to obtain a fit for purpose reservoir model. Multiple Point Statistics (MPS) is a relatively novel pixel-based geostatistical approach that does not use variogram models but, instead, utilizes patterns from training images (TIs) that approximate trends of—and spatial interrelationships among—geological attributes, in this case PRTs (Strebelle, 2002; Strebelle and Levy, 2008). It is best utilized where data density is low and patterns are mostly based on analogs and concepts or forward modeling or, where PRTs are well defined, their spatial trends and interrelationships relatively well-constrained and linked to geological attributes.

Still referring to FIG. 17, step 1105 analyzes Variogram Lengths, generates a Probability Cube and runs the PRT Distribution for the stochastic case. When selecting a stochastic approach based on data density and scale of heterogeneity considerations, the workflow follows standard procedures. Those include the determination of variogram lengths for all PRTs, the generation of probability maps and vertical proportion curves that include necessary editing using trends from analogs, as well as the generation of conceptual models and forward modeling results. Finally, variograms are convolved with the probability cube and proportion curve to generate PRT distributions. Iterations between the different steps are critical to review the results. Several variations on variogram methods are available, each with a specific purpose and a possible "match" with the observed geological attributes. Object based (Boolean) modeling allows the introduction of objects such as channels or mounds in stochastic models but generally limits the conditioning to proportions. Sequential indicator (integer values of facies or PRTs) simulation (SIS) combines variograms and target proportions when multiple trends are believed to control distributions. Truncated Gaussian simulation (TGS) supports the modeling of parallel facies (or PRT) trends such as observed in prograding deltas or in some carbonate systems alike.

Still referring to FIG. 17, step 1107 designs a Training Image (TI), and generates a probability of PRT distribution (Probability Cube) and generates the PRT Distribution for the MPS case. One or more training images capture all 3D spatial trends and interactions between PRTs and is convolved with a PRT probability cube while conditioning to a vertical PRT proportion curve and hard PRT data at the well locations. The flexibility of the method lies in the design of the training image as well as the determination of the probability cube which both can be modified by the geologist to realistically mimic expected trends from analogs or concepts. The vertical proportion curve (VPC) defines the proportions of PRT vertically in the reservoir. The VPC curve may be adjusted to generate realistic proportions supported by analogs and conceptual models.

Still referring to FIG. 17, step 1109 performs the QC and Evaluation of the PRT Distribution and, if needed, loops back to step 101 of FIG. 1

The distribution of PRTs in the static model is non-unique, and numerous iterations in the design of the training images and probability cube as well as the vertical proportion curve may be required to generate several (high, mid and low) distributions. Dynamic data, such as Production Logs (PLTs), Drill stem test data (DSTs) and wire line formation test (WFT) data may be interrogated to loop back and adjust the distribution and proportions of PRTs that reflect baffles and reservoir intervals In the case where 3D modeling resources are not available, the workflow terminates at Step 113 of FIG. 1. If no dynamic data are available, the workflow terminates at Step 111 of FIG. 1. Acquisition of the dynamic data might trigger the next loop 200 starting over at step 201 of FIG. 2.

Figure 18:
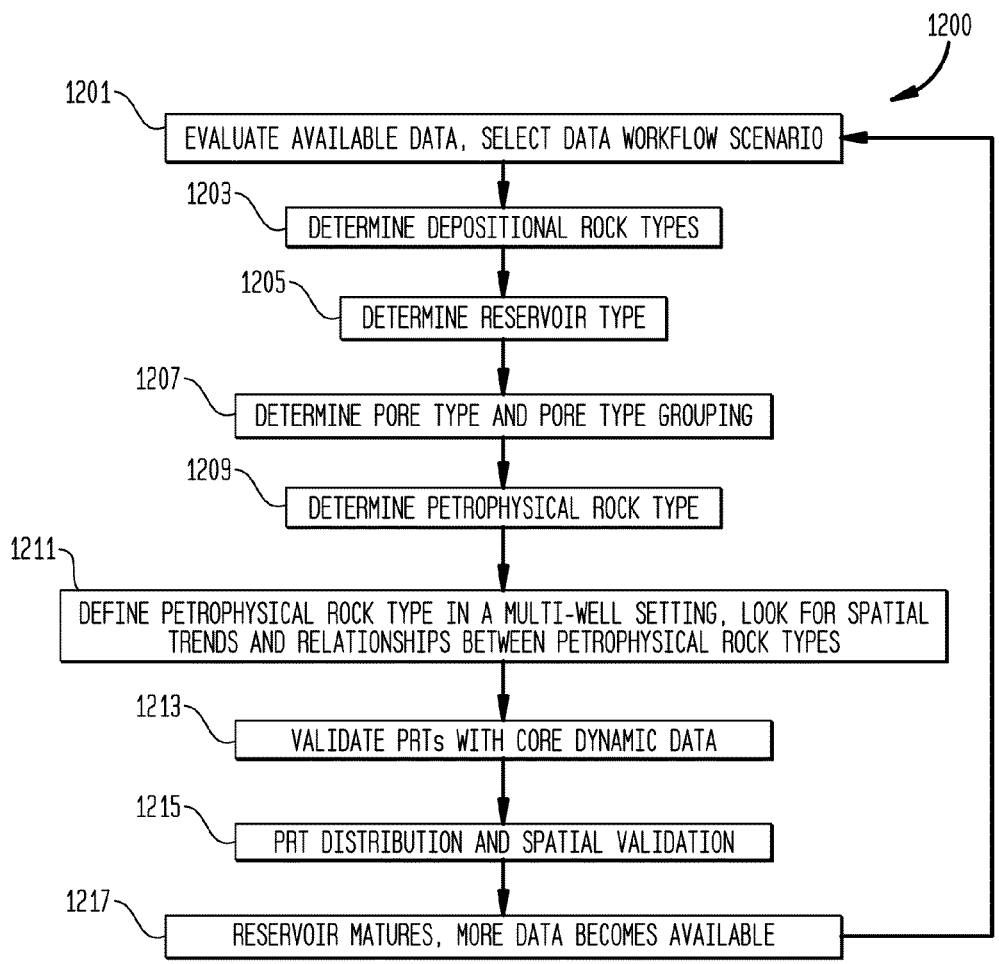
FIG. 18 shows the eight steps of a workflow in a linear arrangement with more detailed descriptions of the steps.

Referring now to FIG. 18, flow chart 1200 shows the eight steps of FIG. 1, that is, the eight major steps of the workflow, in a linear arrangement with longer descriptions than those provided in FIG. 1, along with a ninth step that demonstrates the beginning of a second loop as shown in workflow 200 of FIG. 2.

At step 1201, which corresponds to FIG. 1 step 101, the available data are evaluated, ranked, and a data workflow scenario is selected.

At step 1203, which corresponds to FIG. 1 step 103, Depositional Rock Types are determined. This step may comprise:
  determining DRTs from cores;
  building a DRT catalog and
  predicting DRT values from logs.

At step 1205, which corresponds to FIG. 1, step 105, the Reservoir Type is determined. This step may comprise:
  assessing conformity between DRTs and Flow Indicators;
  assessing Diagenetic Modifiers, and
  assigning Reservoir Type based on relative contribution of DM and fractures on flow.

At step 1207, which corresponds to FIG. 1, step 107, Pore Type and Pore Type Grouping are determined. This step may comprise:
  MICP Core Typing;
  predicting pore Type groupings from PKS data;
  predicting pore Type groupings from logs;
  determining secondary porosity from well log data, and
  combining pore type and secondary porosity for final Pore Type definition.

At step 1209, which corresponds to FIG. 1, step 109, the Petrophysical Rock Types are determined based on permeability barriers, Depositional Rock Types, Diagenetic Modifiers, and Pore Types.

At step 1211, which corresponds to FIG. 1, step 111 Petrophysical Rock Types are defined in a multi-well setting, and spatial trends and relationships between Petrophysical Rock Types are detected.

At step 1213, which corresponds to FIG. 1, step 113, the PRTs are validated with core and dynamic data, and the conformance of the PRTs to dynamic data is evaluated.

At step 1215, corresponds to FIG. 1, step 115 PRT Distribution and spatial validation are performed. This step includes extracting complete spatial interrelation rules and trends for PRTs by mapping PRTs determined in all wells across the field, and determining the optimal geostatistical model.

Step 1217 corresponds to the trigger that causes the loop to begin over with workflow 200 shown in FIG. 2.

The above-described embodiments should be considered as examples of the various embodiments, rather than as limiting the respective scopes thereof. In addition to the foregoing embodiments, review of the detailed description and accompanying drawings will show that there are other embodiments. Accordingly, many combinations, permutations, variations and modifications of the foregoing embodiments not set forth explicitly herein will nevertheless fall within the scope of the various embodiments.

What is claimed is:

1. A computer-implemented method for petrophysical rock typing in an oil or gas reservoir or field, comprising:
  a) selecting a Data Scenario (DS) for the oil or gas reservoir or field based on at least one or more of a well density, well log data, core data, production data, or combinations thereof from the oil or gas reservoir;
  b) determining a plurality of Depositional Rock Types (DRTs) for the oil or gas reservoir or field, each DRT being based upon one or more depositional attributes associated with the oil or gas reservoir or field;
  c) determining a Diagenetic Modification (DM) from a plurality of diagenetic modifiers or primary textures associated with the plurality of DRTs;

d) selecting a predefined Reservoir Type (RT) based on the Diagenetic Modification (DM) and corresponding to the plurality of DRTs and associated with the oil or gas reservoir or field;

e) determining at least one pore type based on at least one or more of the core data, mercury capillary injection pressure (MICP) data, well log data, or combinations thereof from the oil and gas reservoir; and f) transforming the plurality of DRTs, the Diagenetic Modification (DM), and the at least one pore type into a plurality of Petrophysical Rock Types (PRTs) associated with the RT, wherein at least one of (a) through (f) is performed on a computer, wherein the computer comprises a computer processor and a storage medium and a program recorded thereon for directing the computer processor to facilitate the implementation of (a) through (f).

2. The method of claim 1, wherein the predefined RT is one of a Type I RT, a Type II RT, or a Type III RT, the Type I RT being associated with rocks that have not been substantially modified since deposition and where fluid flow therethrough is controlled principally by the depositional attributes thereof, the Type III RT being associated with rocks that have undergone diagenesis since deposition and where fluid flow therethrough is controlled principally by diagenetic properties associated therewith, the Type II RT being associated with rocks that are hybrids of the Type I RT and the Type III RT.

3. The method of claim 1, wherein determining the at least one pore type is based on well log data.

4. The method of claim 1, wherein the plurality of PRTs are identified by logging surveys.

5. The method of claim 1, wherein the plurality of PRTs are linked to geological attributes.

6. The method of claim 5, wherein the geological attributes include primary texture and diagenetic modifications.

7. The method of claim 1, further comprising determining and associating a Nelson fracture type with the RT.

8. The method of claim 7, further comprising determining whether the fracture type is a type a fracture, a type b fracture, or a type c fracture.

9. The method of claim 1, wherein at least some of the plurality of PRTs are determined using well log data derived from multiple wells in the reservoir or field.

10. The method of claim 1, further comprising validating at least some of the PRTs with core data.

11. The method of claim 1, further comprising validating at least some of the PRTs with dynamic data.

12. The method of claim 1, further comprising determining a spatial distribution of the PRTs in a 3D model of the RT.

13. The method of claim 1, wherein the DS is further determined by ranking the data.

14. The method of claim 1, further comprising determining diagenetic attributes associated with the RT.

15. The method of claim 1, further comprising determining the RT is a Type I RT when the DM is low.

16. The method of claim 1, further comprising determining the RT is a Type III RT when the DM is high.

17. The method of claim 1, further comprising determining the RT is a Type II RT when the DM is neither high nor low.

18. The method of claim 1, further comprising assessing conformity between the plurality of DRTs and flow indicators associated therewith by comparing the plurality of DRTs to porosity permeability saturation data (PKS).

19. The method of claim 18 wherein comparing the plurality of DRTs to dynamic data further comprises comparing the plurality of DRTs to at least one of production log data (PLTs), drill stem test data (DSTs), and wireline formation test data (WFTs).

20. The method of claim 1, wherein determining the at least one pore type uses mercury injection capillary pressure analysis (MICP).

21. The method of claim 20, further comprising combining pore types from the MICP with vug or fractures.

22. The method of claim 21, wherein the vug or fracture data are based at least partially on well log data.

23. The method of claim 20, further comprising grouping MICP-derived data to obtain Pore Type Groups (PTGs).

24. The method of claim 23, wherein PTGs are predicted by using porosity-permeability-saturation data (PKS) and multivariate statistical methods.

25. The method of claim 23, wherein PTGs are predicted by using well log data.

26. The method of claim 1, wherein determining the at least one pore type further comprises nuclear magnetic resonance analysis (NMR).

27. The method of claim 1, wherein determining the at least one pore type further comprises using core descriptions and thin sections.

28. The method of claim 1, wherein determining the at least one pore type further comprises determining secondary porosity.

29. The method of claim 28, wherein determining secondary porosity further comprises using well log data derived from nuclear magnetic resonance (NMR) measurements, formation microscanner (FM) measurements, and acoustic measurements.

30. The method of claim 28, further comprising validating secondary porosity determinations with core images or pore scale modeling based on computer tomography (CT) scans.

31. The method of claim 1, wherein the plurality of PRTs is further defined according to at least one of permeability barriers, DRTs, DMs and pore types.

32. The method of claim 1, further comprising validating the plurality of PRTs by comparing at least one of the PRTs to pressure profiles from formation testers or transient pressure test results.

33. The method of claim 1, further comprising computing and mapping a spatial variation of PRTs across at least portions of the field or reservoir.

34. The method of claim 33, wherein statistical methods are employed to compute and map the spatial variation of the PRTs.

35. The method of claim 1, further comprising repeating all of the steps when additional data becomes available.

36. A system for petrophysical rock typing in an oil or gas reservoir or field, comprising:

a. a non-transitory data source storing computer modules;

b. a user interface;

c. at least one computer processor configured to communicate with the non-transitory data source and the user interface and to execute said computer modules, the computer modules configured for:

selecting a Data Scenario (DS) for the oil or gas reservoir or field based on at least one or more of a well density, well log data, core data, production data, or combinations thereof;

determining a plurality of Depositional Rock Types (DRTs) for the reservoir or field, each DRT being based upon one or more depositional attributes associated with the oil and gas reservoir or field;

determining a Diagenetic Modification (DM) from a plurality of diagenetic modifiers or primary textures associated with the plurality of DRTs;

selecting a predefined Reservoir Type (RT) based on a Diagenetic Modification (DM) and corresponding to the plurality of DRTs and associated with the oil or gas reservoir or field;

determining at least one pore type based on at least one or more of the core data, mercury capillary injection pressure (MICP) data, well log data, or combinations thereof from the oil and gas reservoir; and determining a plurality of Petrophysical Rock Types (PRTs) associated with the RT based on the plurality of DRTs, the Diagenetic Modification (DM), and the at least one pore type, a plurality of Petrophysical Rock Types (PRTs) associated with the RT.

37. The system of claim 36, wherein the predefined RT is one of a Type I RT, a Type II RT, or a Type III RT, the Type I RT being associated with rocks that have not been substantially modified since deposition and where fluid flow therethrough is controlled principally by the depositional attributes thereof, the Type III RT being associated with rocks that have undergone diagenesis since deposition and where fluid flow therethrough is controlled principally by diagenetic properties associated therewith, the Type II RT being associated with rocks that are hybrids of the Type I RT and the Type III RT.

38. The system of claim 36, wherein the computer modules are further configured for determining and associating a Nelson fracture type with the RT.

39. The system of claim 36, wherein the computer modules are further configured for validating the plurality of PRTs by comparing at least one of the PRTs to pressure profiles from formation testers or transient pressure test results.

40. The system of claim 36, wherein the computer modules are further configured for computing and mapping a spatial variation of PRTs across at least portions of the field or reservoir.

41. The system of claim 40, wherein statistical methods are employed to compute and map the spatial variation of the PRTs.

* * * * *